United States Patent [19]

Schultz

[11] 4,091,038
[45] May 23, 1978

[54] PRODUCTION OF DIHYDROXYDIPHENYL ALKANES

[75] Inventor: Robert G. Schultz, St. Louis, Mo.

[73] Assignee: Monsanto Company, St. Louis, Mo.

[21] Appl. No.: 780,738

[22] Filed: Mar. 24, 1977

[51] Int. Cl.$^2$ ............................................. C07C 29/00
[52] U.S. Cl. .................................................... 568/729
[58] Field of Search ......................... 260/619 B, 624 C

[56] References Cited

U.S. PATENT DOCUMENTS

| 2,091,483 | 8/1937 | Olin ................................... 260/624 R |
| 2,134,711 | 11/1938 | Flett ................................... 260/624 C |
| 2,567,848 | 9/1951 | Kooyman ........................... 260/624 C |
| 2,900,418 | 8/1959 | Huett et al. ........................ 260/624 C |
| 3,463,824 | 8/1969 | Velling .............................. 260/624 C |

OTHER PUBLICATIONS

Nosalevich et al., "Vestr. Khar'kov. Politekh. Inst." (Ukrain), No. 60 (1971), 61–64.

*Primary Examiner*—Joseph E. Evans
*Attorney, Agent, or Firm*—James C. Bolding; Elizabeth F. Sporar

[57] ABSTRACT

Iodine is employed as a promoter for the reaction between phenol and a 1,2-dihaloethane wherein the halogen is chlorine, bromine or iodine using a zinc-containing catalyst to produce dihydroxydiphenylethanes, especially the 4,4'-isomer.

11 Claims, No Drawings

PRODUCTION OF DIHYDROXYDIPHENYL ALKANES

BACKGROUND OF THE INVENTION

The present invention relates to the preparation of dihydroxydiphenyl alkanes by the reaction of phenol and dihaloalkanes. More particularly, it relates to an improved method for preparing 4,4'-dihydroxydiphenylethane sometimes referred to as bisphenol E.

Dihydroxydiphenyl alkanes, also known as bisphenols, are useful in the production of high polymers, epoxy resins and high-molecular weight thermoplastic condensates as well as intermediates in organic syntheses, the best known of such compounds, bisphenol A, being widely employed. It has been suggested in an article by I. M. Nosalevich et al entitled "Preparation of dihydroxydiphenylalkanes by the alkylation of phenol by dihaloalkanes" [(Vestn. Khar'kov. Politekh. Inst. 1971, No. 60, 61–4) (Ukrain)] that an increase in the number of technically available dihydroxydiphenyl alkanes would open up possibilities for modification of polymeric materials formed from them. Following this line, these workers have described several methods of preparing dihydroxydiphenyl alkanes among which is that of the direct interaction of phenol with dichloroethane or dibromoethane in the presence of zinc to give the 1,2 - bis (4-hydroxyphenyl) ethane (also known as 4,4'-dihydroxydiphenylethane) and its isomers. It has now been discovered that if the reaction of phenol and a dihaloethane is conducted in the presence of iodine as a promoter with various zinc-containing catalysts, the rate of reaction is significantly increased and lower temperatures can be employed.

SUMMARY OF THE INVENTION

According to the invention, phenol is alkylated with a 1,2-dihaloethane in which the halogen is bromine, chlorine or iodine in at least the stoichimetric proportions of 2:1 in contact with a zinc-containing catalyst at a temperature from about 125° to about 225° C and in the presence of iodine as a promoter for the reaction.

DESCRIPTION OF THE PREFERRED EMBODIMENTS

The process of the invention is conveniently carried out in any apparatus of the type suitable for carrying out chemical reactions in the liquid phase using a solid catalyst, i.e., in a slurry-type reactor, or the liquid reactants can be pumped through a fixed bed of the catalyst. The reaction may be conducted as a batch or continuous operation.

Reactant mole ratios of the phenol to dihaloethane employed may vary from the stoichiometric ratio of 2:1 to as high as 10:1. Preferably, however, phenol-dihaloethane mole ratios in the range from 2:1 to 4:1 are employed.

Suitable catalysts for the reaction include zinc metal and compounds of zinc such as zinc oxide and halides and mixtures thereof or, for example, the acetates, nitrates, carbonates and the like of zinc and mixtures thereof when deposited upon suitable supports. Zinc oxide itself or mixtures thereof with zinc salts constitute the preferred catalysts with a mixture of zinc bromide and zinc oxide especially preferred. In fact, the latter combination provides distinct advantages when employed for the reaction.

Other metal salts and oxides such as those of iron, copper, rhodium and palladium some of which are themselves catalytic can also be employed in admixture with the zinc compounds and in some cases, provide certain advantages such as operation at lower reaction temperatures. The suitable catalysts may be supported on materials such as silica gel, alumina, and the like, if desired. The supported catalysts remain active for relatively long periods of time and are advantageous in that they do not require a zinc removal step in the process. A particularly suitable supported catalyst is ZnO on silica gel.

The amount of catalyst employed generally may vary from about 0.001 to about 2.0 moles per mole of dihaloethane; preferably, an amount from about 0.01 to about 1 mole per mole of the dihaloethane reactant is employed.

The temperature at which the reaction proceeds varies in general from about 125° to about 225° C depending upon the particular catalyst employed and the particular dihaloethane reacted. The use of the higher temperatures tends to be detrimental to obtaining the desired 4,4'-isomer. With the same catalyst, lower temperatures, e.g., 125° - 150° C, are suitable with dibromoethane as the alkylating agent whereas with dichloroethane as reactant, higher temperatures, e.g., 175° C and up, are generally required. One of the major advantages of the iodine promoter of the present invention is that it provides for alkylation with dichloroethane at low enough temperatures to preclude the use of superatmospheric pressures. Preferably, with the promoter present the temperature is generally maintained between 125° and 150° C.

Iodine is introduced as a promoter in the reaction in its molecular form. The iodide ion, I$^-$, charged as KI for example, while it may have some slight observable effect with certain catalysts such as ZnO, is not generally effective in promoting the reaction. The iodine promoter is readily introduced by charging iodine crystals to the reactor or by bubbling or sparging gaseous iodine directly into the reactor. Amounts in the range from about 0.001 to about 1 mole per mole of dihaloethane are satisfactory while amounts from about 0.01 to about 0.05 mole per mole of dihaloethane are preferred particularly with the zinc oxide catalyst.

The 4,4'-dihydroxydiphenylethane can be readily recovered from the reaction mixture by conventional techniques. If the catalyst is present in solid form, it is removed by filtration. If the catalyst is in the dissolved state it is extracted or washed out with water. The catalyst-free reaction mixture is then distilled to strip out any unreacted dihaloethane and excess phenol. A fraction rich in the 4,4'-isomer can then be recovered from the remaining mixture by adding an amount by weight equal to said residue of a selective solvent such as dichloroethane, dibromoethane or chlorocyclohexane and cooling to effect crystallization. The crystalline fraction is separated by filtration and can be purified by continued recrystallization with an acetic acid-water mixture, a mixture of alcohols, dichloroethane or other suitable solvent to 4,4'-isomer of the desired purity.

In order to increase yield of the desired product, the filtrate containing bisphenol-type oligomers and/or tars can be subjected to transalkylation and/or isomerization. This is effected by heating it at a temperature from about 150° to about 250° C in contact with a mixture of phenol and zinc bromide or zinc chloride and the corresponding hydrogen halide and then recovering the isomer from the resulting mixture.

In an alternative method, all the isomers can be recovered as a fraction from the stripped residue by treating the residue with acetone or other suitable solvent and then treating the solution with a decolorizing agent such as activated carbon to absorb the oligomers and/or tars and obtain a pale yellow solution of mixed dihydroxydroxydiphenylethane isomers from which the solvent can then be evaporated. The 4,4'-isomer may be recovered from the mixture in substantially the same manner as described above. The residual isomer mixture can then be subjected to an isomerization step to increase the content of the 4,4'-isomer therein by heating it with phenol in contact with zinc bromide and treating with HBr or with zinc chloride in conjunction with HCl. Recovery of the isomer can then be effected by crystallization and re-crystallization to the desired purity.

The invention is illustrated in the following examples which are not to be considered as limiting it in any manner.

EXAMPLE

A series of runs was made in which phenol and either 1,2-dibromoethane or 1,2-dichloroethane were reacted using either zinc bromide or zinc oxide as catalyst. The phenol was melted and 37.6g (0.40 mole) was charged to 100-cc, four-necked flask. A zinc oxide or zinc bromide catalyst was added to the flask. A thermowell, sampling port, reflux condenser and dropping funnel were connected to the flask and the flask contents was heated to reaction temperature while subjected to magnetic stirring. Then 0.1 mole of either 1,2-dibromoethane (8.6cc, 18.8g) or 1,2-dichloroethane (7.8cc, 9.8g) was added slowly through the dropping funnel. The mixture was stirred at reaction temperature over a given period of time, with the effluent HBr or HCl given off being directed through tubing connected to the reflux condenser into a bubbler containing standard sodium hydroxide for collection of the off-gas.

At the end of the reaction period, the reaction mixture was analyzed by gas chromatographic means to determine the amount of dihydroxydiphenylethanes (DDE'S) present. It was then subjected to acetylation by heating at 100° C with an excess of acetic anhydride and the acetylated product was again analyzed by gas chromatographic means to determine the percentage (by wt) of the 4,4'-isomer present in the acetylated DDE'S of the reaction mixture. In certain of the runs, iodine was introduced by adding a few crystals of this element to the reaction mixture. The conditions for the various runs and the results obtained are presented in the table below, with Part A of the table summarizing the runs made with 1,2-dibromoethane and Part B those made with 1,2-dichloroethane.

It will be seen by comparing the results in Runs 2 and 5, for example, that with zinc bromide as catalyst, the addition of iodine to the reaction system, even in very small amounts, results in significant acceleration of the rate of reaction. Over a given reaction time at a given reaction temperature, iodine accelerates the reaction rate of phenol alkylation with 1,2-dibromoethane if introduced as $I_2$ but has little significant effect if added to the reaction as $I^-$ for example by the addition of KI. These effects are seen by comparison of Runs 11 – 14 with a zinc bromide catalyst and Runs 15, 21, 25 and 26 with a zinc oxide catalyst among others. With 1,2-dichloroethane as the alkylating agent (Table 1B), the iodine promotes the reaction to the extent that it makes it possible to operate at lower temperature which favor the formation of the desired 4,4'-isomer and preclude the necessity for operation with this dihaloethane under pressure. Similar increases in reaction rate are also demonstrated.

TABLE

A. PHENOL, 4 MOLES; 1,2-DIBROMOETHANE, 1 MOLE

| RUN No | CATALYST Kind | Amt (mole) | IODINE Cmpd | Amt (mole) | REACTION TIME (hr) | TEMPERATURE (° C) | PRODUCT ANALYSIS (AREA %) Dibromoethane | Phenol | Intermediates | DDE'S | 4,4'-Isomer |
|---|---|---|---|---|---|---|---|---|---|---|---|
| 1 | ZnBr$_2$ | 0.2 | None | 0 | 1.5 | 150 | 4.2 | 89.9 | 1.0 | 4.9 | |
| 2 | ZnBr$_2$ | 0.2 | None | 0 | 2.0 | 150 | 4.4 | 87.7 | 1.1 | 6.7 | |
| 3 | ZnBr$_2$ | 0.2 | None | 0 | 6 | 150 | 0.8 | 78.9 | 1.5 | 18.8 | 17.2 |
| 4 | ZnBr$_2$ | 0.2 | I$_2$ | 0.05 | 2.25 | 150 | 0.4 | 84.3 | 4.5 | 10.9 | 13.8 |
| 5 | ZnBr$_2$ | 0.2 | I$_2$ | 0.10 | 2.0 | 150 | TR | 84.6 | 4.7 | 10.7 | 14.0 |
| 6 | ZnBr$_2$ | 0.2 | I$_2$ | 0.25 | 1.75 | 150 | 0 | 82.2 | 4.4 | 13.4 | 15.4 |
| 7 | ZnBr$_2$ | 0.2 | I$_2$ | 0.5 | 1.25 | 150 | 0 | 84.2 | 2.7 | 13.1 | 15.9 |
| 8 | ZnBr$_2$ | 0.2 | I$_2$ | 0.5 | 2.0 | 150 | 0 | 82.8 | 3.9 | 13.3 | 14.6 |
| 9 | ZnBr$_2$ | 0.2 | I$_2$ | 0.5 | 4 | 125 | 0.7 | 85.4 | 3.0 | 11.0 | 15.9 |
| 10 | ZnBr$_2$ | 0.2 | I$_2$ | 0.5 | 6.5 | 100 | 5.9 | 92.1 | 0.6 | 1.4 | 12.5 |
| 11 | ZnBr$_2$ | 0.2 | I$_2$ | 0.5 | 1.25 | 150 | 0 | 84.1 | 2.6 | 13.3 | |
| 12 | ZnBr$_2$ | 0.2 | I$^-$ | 0.5 | 1.25 | 150 | 3.3 | 90.8 | 1.3 | 4.6 | |
| 13 | ZnBr$_2$ | 0.2 | I$^-$+I$_2$ | 0.25 + 0.25 | 1.25 | 150 | 0.8 | 88.2 | 1.3 | 9.7 | |
| 14 | ZnBr$_2$ | 0.2 | None | 0 | 1.25 | 150 | 4.6 | 91.1 | 0.9 | 3.3 | |
| 15 | ZnO | 0.2 | None | 0 | 1.25 | 150 | 4.5 | 89.9 | 1.1 | 4.5 | |
| 16 | ZnO | 0.2 | None | 0 | 3.25 | 150 | 0.9 | 79.3 | 1.7 | 18.1 | 16.4 |
| 17 | ZnO | 0.2 | I$_2$ | 0.01 | 1.75 | 150 | 1.4 | 81.5 | 2.9 | 14.2 | 18.2 |
| 18 | ZnO | 0.2 | I$_2$ | 0.05 | 1.25 | 150 | 0.5 | 81.9 | 3.9 | 13.8 | 14.2 |
| 19 | ZnO | 0.2 | I$_2$ | 0.10 | 1.25 | 150 | 0.4 | 82.1 | 3.8 | 13.8 | 16.8 |
| 20 | ZnO | 0.2 | I$_2$ | 0.50 | 0.75 | 150 | 0 | 84.2 | 3.1 | 12.6 | 16.7 |
| 21 | ZnO | 0.2 | I$_2$ | 0.50 | 0.50 | 150 | 0.6 | 84.6 | 2.3 | 16.6 | 16.9 |
| 22 | ZnO | 0.2 | I$_2$ | 0.50 | 2.25 | 125 | 1.6 | 87.7 | 2.1 | 8.6 | 16.2 |
| 23 | ZnO | 0.4 | None | 0 | 4.0 | 125 | 5.8 | 94.2 | 0 | 0 | |
| 24 | ZnO | 0.2 | I$_2$ | 0.5 | 3.25 | 100 | 4.7 | 89.1 | 0.2 | 6.1 | 14.0 |
| 25 | ZnO | 0.2 | I$^-$ | 0.5 | 1.25 | 150 | 3.3 | 92.4 | 1.0 | 5.3 | |
| 26 | ZnO | 0.2 | I$^-$+I$_2$ | 0.25 + 0.25 | 1 | 150 | 1.3 | 88.5 | 1.0 | 9.2 | 14.5 |
| 27 | ZnO | 0.05 | I$_2$ | 0.10 | 3 | 150 | 1.1 | 87.8 | 1.5 | 9.6 | 13.8 |

B. PHENOL, 4 MOLES; 1,2-DICHLOROETHANE, 1 MOLE

| RUN No | CATALYST Kind | Amt (mole) | IODINE Cmpd | Amt (mole) | REACTION TIME (hr) | TEMPERATURE (° C) | PRODUCT ANALYSIS (AREA %) Dichloroethane | Phenol | Intermediates | DDE'S | 4,4'-Isomer |
|---|---|---|---|---|---|---|---|---|---|---|---|

TABLE-continued

| | | | | | | | | | | |
|---|---|---|---|---|---|---|---|---|---|---|
| 1 | ZnBr$_2$ | 0.2 | None | 0 | 6 | 130 | 6.2 | 93.8 | 0 | 0 | |
| 2 | ZnBr$_2$ | 0.2 | I$_2$ | 0.5 | 5.5 | 130 | 4.3 | 92.6 | 1.8 | 1.3 | 15.6 |
| 3 | ZnO | 0.2 | None | 0 | 6 | 130 | 5.5 | 93.9 | 0.5 | 0 | |
| 4 | ZnO | 0.2 | I$_2$ | 0.5 | 6 | 130 | 2.6 | 86.1 | 2.8 | 8.6 | 15.0 |

What is claimed is:

1. A process for producing dihydroxydiphenylethanes which comprises reacting phenol with a 1,2-dihaloethane in which the halogen is chlorine, bromine or iodine in at least the stoichiometric proportions of 2:1 in contact with a zinc-containing catalyst at a temperature from about 125° to 225° C and in the presence of iodine as promoter for the reaction.

2. The process of claim 1 wherein the mole ratio of phenol to dihaloethane is in the range from about 2:1 to about 4:1.

3. The process of claim 2 wherein said temperature is in the range from about 125° to about 150° C.

4. The process of claim 2 wherein the amount of iodine promoter is in the range from about 0.001 to about 1.0 mole per mole of dihaloethane.

5. The process of claim 3 wherein the amount of said iodine promoter is in the range from about 0.01 to about 0.05 mole per mole of the dihaloethane.

6. The process of claim 5 wherein said dihaloethane is 1,2-dibromoethane.

7. The process of claim 5 wherein said dihaloethane is 1,2-dichloroethane.

8. The process of claim 6 wherein said zinc-containing catalyst is zinc bromide.

9. The process of claim 6 wherein said zinc-containing catalyst is zinc oxide.

10. The process of claim 7 wherein said zinc-containing catalyst is zinc bromide.

11. The process of claim 7 wherein said zinc-containing catalyst is zinc oxide.

* * * * *